(12) United States Patent
Spartz

(10) Patent No.: US 12,053,755 B2
(45) Date of Patent: Aug. 6, 2024

(54) METHOD AND SYSTEM FOR GENERATING INTERFERENCE SPECTRA FOR LOW DETECTION LIMITS USING REACTOR

(71) Applicant: MLS ACQ, Inc., East Windsor, CT (US)

(72) Inventor: Martin L. Spartz, Ellington, CT (US)

(73) Assignee: MLS ACQ, INC., East Windsor, CT (US)

( * ) Notice: Subject to any disclaimer, the term of this patent is extended or adjusted under 35 U.S.C. 154(b) by 416 days.

(21) Appl. No.: 17/119,297

(22) Filed: Dec. 11, 2020

(65) Prior Publication Data
US 2021/0178352 A1 Jun. 17, 2021

Related U.S. Application Data

(60) Provisional application No. 62/946,859, filed on Dec. 11, 2019.

(51) Int. Cl.
| | |
|---|---|
| *B01L 3/00* | (2006.01) |
| *B01F 23/00* | (2022.01) |
| *B01F 23/41* | (2022.01) |
| *B01F 101/23* | (2022.01) |
| *B01J 15/00* | (2006.01) |
| *B23Q 17/24* | (2006.01) |
| *C12M 1/34* | (2006.01) |
| *C12Q 1/18* | (2006.01) |
| *G01N 21/3504* | (2014.01) |
| *G01N 21/3577* | (2014.01) |
| *G01N 21/359* | (2014.01) |
| *G01N 21/39* | (2006.01) |

(Continued)

(52) U.S. Cl.
CPC ........ *B01J 15/005* (2013.01); *G01N 21/3504* (2013.01); *G01N 27/622* (2013.01); *G01N 30/06* (2013.01); *H01J 49/0422* (2013.01); *G01N 27/4162* (2013.01); *G01N 2030/025* (2013.01)

(58) Field of Classification Search
CPC ....... B01J 15/005; B01J 8/02; G01N 21/3504; G01N 27/622; G01N 30/06; G01N 27/4162; G01N 2030/025; G01N 21/33; G01N 33/0024; G01N 2021/3595; G01N 2021/399; H01J 49/0422
See application file for complete search history.

(56) References Cited

U.S. PATENT DOCUMENTS

| | | | | |
|---|---|---|---|---|
| 2,976,414 A | * | 3/1961 | Warncke | G01N 21/3504 250/341.1 |
| 9,606,088 B2 | | 3/2017 | Spartz et al. | |

(Continued)

FOREIGN PATENT DOCUMENTS

| | | | | |
|---|---|---|---|---|
| CN | 102692398 A | * | 9/2012 | G01N 21/3504 |

OTHER PUBLICATIONS

Model 49i; Instruction Manual; UV Photometric O3 Analyzer Part No. 102434-00; Sep. 25, 2017.

(Continued)

*Primary Examiner* — Jennifer Wecker
*Assistant Examiner* — Oyeleye Alexander Alabi
(74) *Attorney, Agent, or Firm* — Michael Best & Friedrich LLP

(57) ABSTRACT

A gas analysis system and method with a spectrometer, such as a Fourier transform infrared spectrometer, utilizing a reactor, such as a catalytic reactor, for providing reference spectra.

14 Claims, 8 Drawing Sheets

(51) Int. Cl.
  *G01N 21/45*   (2006.01)
  *G01N 21/64*   (2006.01)
  *G01N 27/622*  (2021.01)
  *G01N 30/06*   (2006.01)
  *G01N 33/50*   (2006.01)
  *G01N 33/68*   (2006.01)
  *H01J 49/04*   (2006.01)
  *G01N 27/416*      (2006.01)
  *G01N 30/02*       (2006.01)

(56) References Cited

U.S. PATENT DOCUMENTS

| | | |
|---|---|---|
| 10,054,486 B2 | 7/2018 | Spartz et al. |
| 10,295,517 B2 | 5/2019 | Birks et al. |
| 10,408,746 B2 | 9/2019 | Spartz et al. |
| 11,187,585 B2 | 11/2021 | Spartz |
| 2015/0260695 A1* | 9/2015 | Spartz ................ G01N 30/8641 |
| | | 250/339.01 |
| 2018/0252639 A1* | 9/2018 | Spartz .................. G01N 21/643 |
| 2020/0116569 A1 | 4/2020 | Spartz |
| 2022/0187201 A1 | 6/2022 | Spartz |

OTHER PUBLICATIONS

ThermoScientific, "Model 49i Instruction Manual, UV Photometric O3 Analyzer Part No. 102434-00", Sep. 25, 2017, 314 pages.

\* cited by examiner

METHOD AND SYSTEM FOR GENERATING INTERFERENCE SPECTRA FOR LOW DETECTION LIMITS USING REACTOR

RELATED APPLICATIONS

This application claims the benefit under 35 USC 119(e) of U.S. Provisional Application No. 62/946,859, filed on Dec. 11, 2019, which is incorporated herein by reference in its entirety.

BACKGROUND OF THE INVENTION

U.S. patent application Ser. No. 16/653,689, filed on Oct. 15, 2019, by Spartz, now U.S. Pat. Pub. No. US 2020/0116569 A1, which is incorporated herein by this reference (hereinafter Spartz patent), describes a Fourier transform infrared (FTIR) spectrometer for low level gas detection of chemicals such as Formaldehyde and Ethylene Oxide. In particular, it discloses FTIR spectrometers employing optical filters in their interferometers for improving performance by generating bandlimited interferograms.

Nevertheless, spectral interferences can still be an issue for very low detection levels. Generally, infrared measurements are managed by having a precise library of pure component calibration spectra. The best matches normally achieved between a library calibration spectrum of a given pure component and a sample spectrum of that pure component are only about 1% of the intensity, however. The difference between the sample spectrum and the calibration spectrum is called the residual spectrum. In most cases, the residual spectrum is about 1 to 2% of the sample intensity. If an interference feature has an absorption of 0.10 abs, the best residual achievable would be ~0.001 abs. On the other hand, if the calibration spectrum is collected by the same instrument, the best matches can be 0.1% or ~0.0001 abs. Even this is not good enough if the analyte of interest is 100's, 1,000's, 10,000's, or 100,000's times smaller than the interfering sample matrix, however.

In the past, ultraviolet (UV) oxidation has been used to remove or convert an analyte to another compound to make it possible to measure. In one case, a cell called PAPA was developed. PAPA stands for Photo Assisted Pollution Analysis. See also U.S. Pat. No. 10,408,746 in which a furnace is used to convert reduced sulfur present in food-grade carbon dioxide to sulfur dioxide so that it can be better detected by an FTIR.

SUMMARY OF THE INVENTION

When attempting to measure compounds with features many orders of magnitude lower than one or more an interfering specie, a better spectral interference method is required for accurate analysis to limit biases from those interferences. The best spectral match achievable on any absorption-based spectrometer is an interference spectrum that is measured on the same instrument, at the same concentration, and in a similar, recent time frame (potentially same day, week or month).

Consider the problem of measuring ethylene oxide (EO) at single digit parts per billion (ppb) levels for continuous process abatement exhaust (CEM) and at parts-per-trillion (ppt) levels for ambient air monitoring. 1 ppb of ethylene oxide at 1 atmosphere (atm) pressure, at 150° C. and collected at 2×8 cm$^{-1}$ resolution in a 5.11 meter gas cell only has an infrared absorption feature of 2.5 µAbs units or 16,000 times less than a 2% water (common in air) absorption feature or 0.04 abs in that region.

In general, the objectives include one or more of the following: to have a procedure and/or technology to determine the exact interference spectra of the current or near current sample, without the necessity of collection of new pure component calibration spectra; to find a process to remove the analyte(s) of interest from the sample stream, without changing the sample matrix; to remove the analytes using a simple procedure or one that could be automated by a continuous monitoring system for process, environmental or IH (industrial hygiene–ambient air); to produce a switched reaction device that could be attached to any spectrometric system to allow for the switching of the sample (analyte+matrix) stream to sample matrix only stream. This interference spectrum would then be put in the automated analysis, and/or it could be the interference spectrum for future sample spectra.

These techniques are also applicable as a zero mechanism for measuring Chemical Warfare agents. If those agents are reactive, a method to zero a chemical agent detection system is practical.

In addition, these techniques are used to remove an interference if the interferents were more reactive than the analyte of interest and then perform a direct measurement of the analyte without the interference. One example is measuring siloxanes in the presence of numerous oxygenated hydrocarbons present in biogas, where the oxygenated hydrocarbons are removed to perform a direct siloxane measurement.

In more detail, one approach to temporarily remove ethylene oxide or other analyte of interest to obtain requisite interference spectra involves flowing the sample stream through a reactor, such as a heated oxidation catalyst, a hot furnace reactor, UV illumination or photo-ionization, chemical reaction with reagent or other of a switched reaction device. Details of construction and design include a reaction chamber that holds an oxidation catalyst (different catalysts could be used depending on the compound of interest, such as sulfur compounds) or a furnace reactor. In the oxidation catalyst configuration, a heated sample line is ideally incorporated to raise the gas temperature to the catalyst temperature before reaching the catalytic reactor to assure full removal of the analyte. This heated line can be part of the heated oxidation catalyst reactor for design efficiency. An automated valve system is then incorporated to switch between sample (analyte+sample matrix) and sample matrix only. The analysis software executing on the spectrometer controller is used to collect both the sample spectra and interference spectra. The system can then utilize the interference spectra in the analysis matrix. Additionally, the spectrometer controller could also determine when to switch from sample measurement mode to interference measurement mode, most likely by monitoring the magnitude of the residual spectrum between the interference spectra and the sample spectra. The reactor is connected to a sampling system that pulls or pushes the sample through the reactor and then onto the FTIR or other analyzer.

In general, according to one aspect, the invention features a gas analysis system, comprising a spectrometer for analyzing gas, a switched reaction device for selectively providing a sample stream or a reacted sample stream to the spectrometer, and a controller using the reacted sample stream to create interference spectra for analyzing the sample stream.

In different embodiments, the spectrometer analyzes the gas at negative or positive atmospheric pressures.

In one implementation, the switched reaction device simultaneously flows one of the sample stream and the reacted sample stream to the spectrometer and the other one to an exhaust. But, in other cases the streams switched on and off, in an alternating fashion.

Preferably, the reaction device comprises preheater for heating the sample stream before flowing into the reactor.

Different reactors can be used such as a thermal catalytic oxidizer reactor or furnace reactor, UV illumination or photo-ionization reactor, chemical reactor with reagent to remove interference gas(es) and/or analyte(s).

In one mode of operation, the controller operates the system in a batch mode in which interference spectra are collected before and after spectra of the sample stream.

Different spectrometer can be used such as is an infrared absorption spectrometers, mass spectrometers, ion mobility spectrometers, electrochemical sensors, or gas chromatographs.

In general, according to another aspect, the invention features a gas analysis method comprising selectively providing a sample stream or a reacted sample stream to a spectrometer and using the reacted sample stream to create interference spectra for analyzing the sample stream.

The interference spectra might be collected over a limited spectral range such as a spectral range including 2,500-3,500 cm−1 for the detection of EO, for example.

In operation, the interference spectra might be used to analyze the sample stream for a predetermined period of time before then collecting new interference spectra.

In operation, residual spectra between the interference spectra and spectra of the sample stream might be used for determining when to collect new interference spectra.

In general, according to another aspect, the invention features reaction device comprising an input line for receiving a sample stream, an output line for providing gas to a spectrometer, a reactor path including a reactor for reacting gas in the sample stream and provided the reacted sample stream to the output line, and a bypass path for bypassing the reactor to the output line.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

It will be understood that although terms such as "first" and "second" are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Ethylene oxide (EO) is an extremely reactive material that is widely used in the chemical industry as a precursor for many polymeric and chemical processes. Since the two main EO infrared interferences are water and methane, it is possible that its reactivity could be used to remove it from the sample stream and measure the infrared interference spectrum of the sample matrix extremely accurately. Then those accurate interference spectra could be added to the analysis method to predict the EO present in the unreacted, sample stream.

Figure 1:
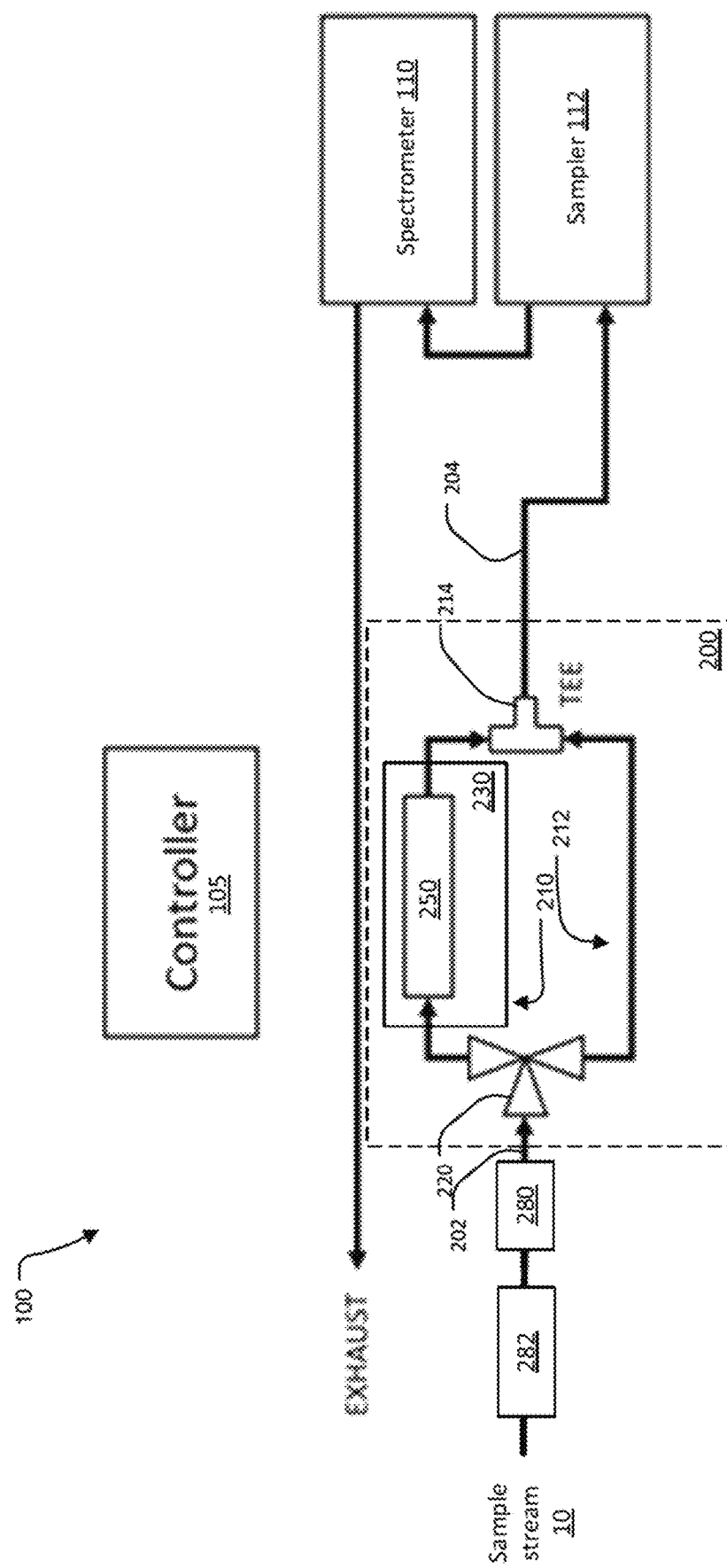
FIG. 1 is a schematic diagram of a gas analysis system of the present invention.

FIG. 1 shows a gas analysis system 100 that has been constructed according to the principles of the present invention.

The system 100 is controlled by a controller 105. And, a spectrometer 110 detects spectra of gases contained in its sample cell, for example, and reports those spectra to the controller 105.

In the current embodiment, the spectrometer 105 is an infrared absorption spectrometer, and particularly a FTIR spectrometer. However, in other embodiments, different infrared absorption spectrometers could be used including dispersive spectrometers and non-dispersive spectrometers such as tunable diode laser absorption spectrometers (TD-LAS), cavity ringdown spectrometers (CRDS) as well as UV and VUV absorption spectrometers.

In addition, spectrometers other than absorption spectrometers could be used, such as mass spectrometers, ion mobility spectrometers, electrochemical sensors and potentially gas chromatographs.

The gas input to the spectrometer 110 is provided by a sampler 112. This sampling pump (in this configuration) pulls the gas from the sample (ambient air or process) filters the gas for particulate matter and pushes the gas onto the spectrometer.

A switched reaction device 200, under control of the controller 105, provides the gas interface between the sample stream 10 and the sampler 112.

The switched reaction device 200 receives the sample stream gas on an input line 202 and supplies gas to the sampler 112 on an output line 204. The switched reaction device 200 includes a reactor path 210 that passes the sample stream gas through a reactor 250 and a bypass path 212 that avoids the reactor 250.

There are a number of ways of implementing the reactor 250. In one example, the reactor is a heated oxidation catalytic reactor. In other example, the reactor is a hot furnace reactor. In still other examples, the reactor is a UV illumination or photo-ionization reactor, chemical reactor with reagent.

In addition, the switched reaction device 200 includes an automated valve system 220 that controls whether gas from the reactor path 210 or from the bypass path 212 is provided to the sampler 112 and then to the spectrometer 110 under control of the controller 105.

In the illustrated example, the automated valve system 220 is on the upstream side of the switched reaction device 200 with a T-junction 214 on the downstream side. Other configurations are possible, however. For example, the sample stream could flow continuously through both the reactor path 210 and the bypass path 212. Then the automated valve system 220 would simply divert the output of one of these paths onto the spectrometer 110. In another example, the automated valve system 220 is on the downstream side of the switched reaction device 200 with a T-junction on the upstream side.

In the case of detecting low-level EO using a FTIR spectrometer, the spectrometer 110 is preferably configured as described in the Spartz patent. To summarize, it uses a narrow band HgCdTe (MCT) or InAs, e.g., a 4 or 5-μm cutoff, that has much higher Detectivity "D*" than standard MCT detectors. D* is the photo sensitivity per unit active area of the detector. In the current embodiment, peak detectivity "D*" of the detector is preferably higher than $1 \times 10^{10}$. Preferably, it is about $1 \times 10^{11}$. This higher D* provides the framework to obtain much higher signal-to-noise spectral data and produce much lower detection limits for compounds with spectral features in the 1 to 5 μm spectral region. An optical filter with a passband of less than 450 $cm^{-1}$, bandpass filters the light received by the FTIR's detector. Typically the passband is smaller such as less than 300 $cm^{-1}$, and its passband is sometimes about 150 $cm^{-1}$. Preferably, the filter 116 is placed in front of the detector. Typically, the center wavelength of the filter's passband is between 3 and 4 μm.

The present oxidative approach employs a switched reaction device 200 with a small catalytic reactor with one or more oxidation catalysts. The switched reaction device 200 includes a heater system 230 that is controlled by the system controller 105 to raise the temperatures of the reactor to the point where EO is consumed but the water and methane (as well as other potential organic material) of the sample matrix pass through unchanged.

The sample stream from the bypass path 212 and reactor stream from the reactor path 210 are configured in parallel paths both leading to the spectrometer 110, such as an FTIR spectrometer. In operation, the input to the FTIR analyzer gas cell is switched back and forth between the sample stream and reactor stream by the controller's operation of the valve system 220 as needed to collect the absorption spectra of the sample and the absorption (interference) spectra of the sample matrix.

In one mode of operation, the spectrometer controller 105 is configured to automatically trigger the switch to the reactor stream when the EO residual error reaches a critical point, such as by control of automated valve system 220.

From previous research it is known that higher molecular weight organic materials oxidize when passed across an oxidation catalyst at temperatures of only 200° C. Due to EO's reactivity, it can be fully removed by a dual oxidation catalyst at temperatures below 125° C. Thus, a very inexpensive catalytic reactor can be built with routine materials and without the need for a high temperature furnace.

In the illustrated embodiment the sampler sampling pump 112 is located downstream of the switched reaction device 200, but in general the sampling pump can be before or after the reaction device.

From experimentation, it appears another optimal configuration would have the incoming sample gas evenly split with half flowing continuously through the bypass channel while the other half is constantly flowing through the reactor channel. A selector valve is then utilized to select the gas stream that is directed to the gas analyzer.

However, if both channels are flowing continuously it is ideal to have the sample pump 112 before the reaction device 200 so constant flows may be maintained for both sample paths. Additionally, higher pressures can be utilized if the sample pump 112 is before the reaction device 200. Up to 60 psig reactor pressures and 5 liters per min flow have been demonstrated as of this writing with excellent EO removal in the oxidizer mode.

To further improve the analysis, it is ideal to more tightly control the moisture concentration in the sample, so its spectral contribution is a constant. This can be accomplished by running the sample through a chiller 280 or similar device prior to reaching the reaction device 200 to maintain the water concentration at a constant vapor pressure based on the chiller temperature. The chiller 280 is preferably operated at temperatures of less than 10° C. to pre-cool the sample stream down to 10° C. or less or possible less than 8° C. or 6° C. Pre-cooling the sample stream 10 down to 4° C. has been demonstrated to allow EO from the sample stream to pass unretained.

If a pressurization pump 282 is utilized, the moisture will naturally condense from the sample as the moisture exceeds its vapor pressure for the temperature of the gas. This pressurization along with a chiller would provide an idealized sample to the analyzer. The water concentration would be at a minimum and constant, while the EO would be compressed and concentrated into the gas cell adding more molecules to measure. In one example, the pressurization pump 282 pressurizes the sample stream 10 under the control of the controller 105 to greater than 2 atm. In some examples, the sample stream 10 is pressurized to greater than 3 atm. And the pressurization is maintained through the system 100 including the sample cell of the spectrometer 110 such that the absorption spectra of the sample and the interference spectra of the sample matrix are obtained at pressures of greater than 2 atm or 3 atm.

Figure 2A:
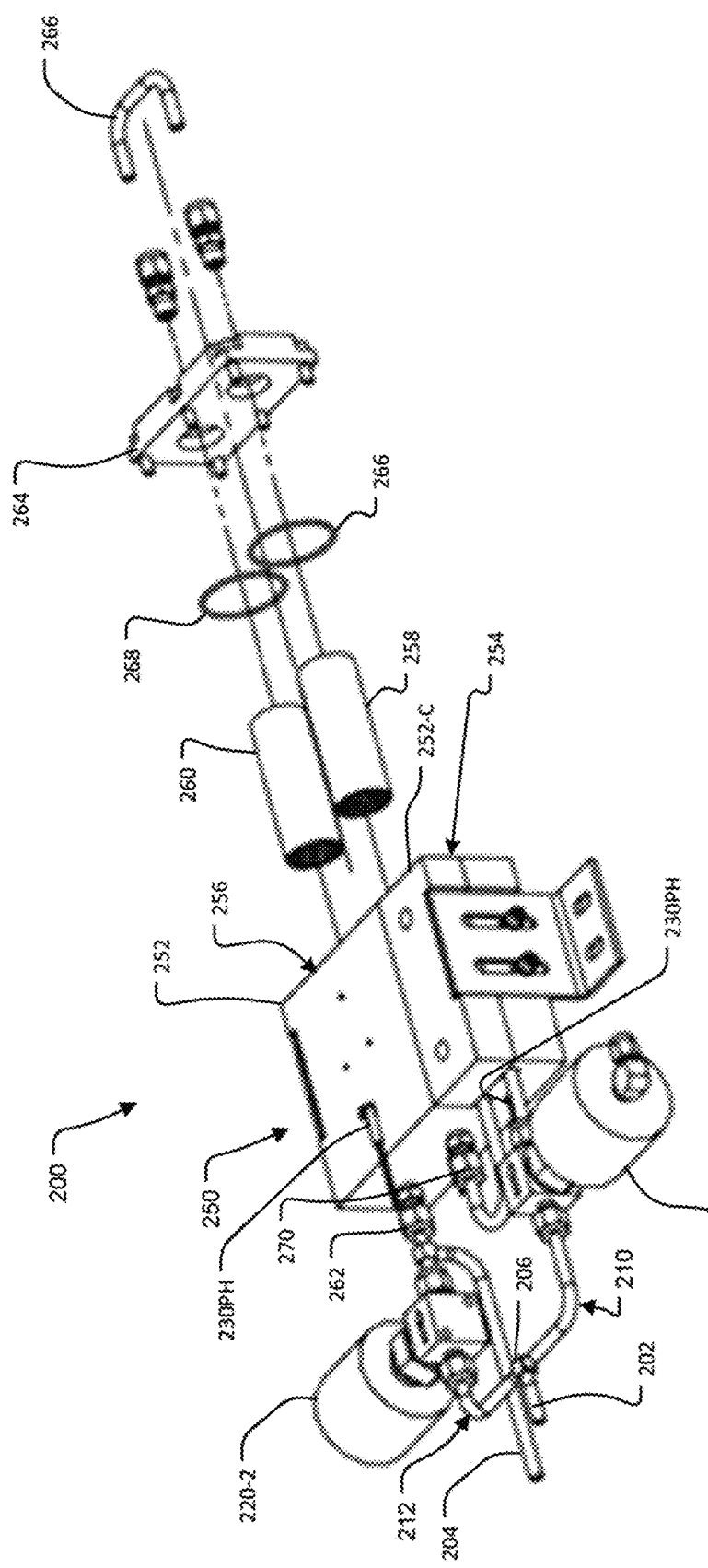
FIGS. 2A and 2B are exploded perspective scale views of a switched reaction device of the invention.
Figure 2B:
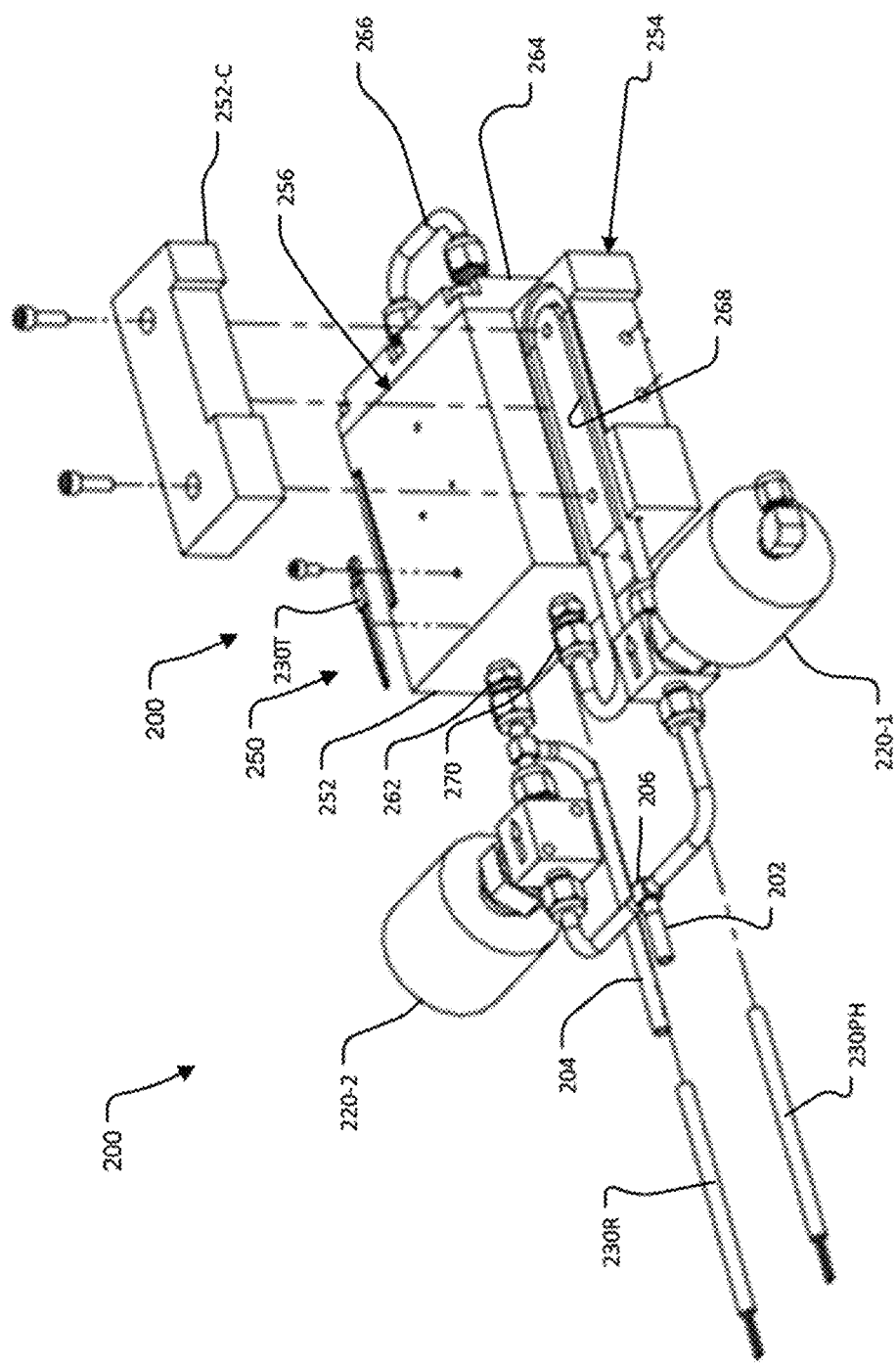

FIGS. 2A and 2B are exploded views of a switched reaction device 200 according to a current embodiment.

The sample stream 10 is received on the input line 202. It is coupled to T-section 206 that divides the sample stream between the reactor path 210 and the bypass path 212.

On the bypass path 212, a bypass valve 220-2 of the automated valve system 220 is operated by the system controller 105 to couple the sample stream to the output line 204.

On the reactor path 210, a reactor valve 220-1 is also operated by the system controller 105 to couple the sample stream into the reactor 250.

The reactor 250 comprises a housing 252 that includes a preheater section 254 in which the incoming sample stream is preheated. A subsequent catalyst section 256 receives the preheated gas from the preheater section 254 and directs the gas through two serial catalyst cores 258, 260, inserted within the housing 252. A U-shaped tubing section 266 couples the gas from the first core 258 to the second core 260. Finally, the gas leaves the reactor 250 via reactor output line 262, which is coupled to device output line 204.

The housing 252 is constructed from an aluminum block with two reaction chamber holes drilled into the distal side of the housing 252 to accommodate the 1×3.5-inch cylindrical catalyst cores 258, 260. The housing has a removable preheater cap 252-C that is bolted to the body of the housing 252. Removal of the cap 252-C exposes the preheater tubing 268 extending through a path formed in the housing.

Ideal catalysts are those platinum catalysts commonly used to remove organic material like formaldehyde emanating from natural gas fired rotary internal combustion engines (RICE).

A sealing plate 264 is bolted to the distal side of the housing 252 sealing the mouths of the first and second reaction chamber holes. Appropriately sized o-rings 266, 268 prevent the sample stream from flowing around the catalyst cores 258, 260 as it passes through the two reaction chambers.

In the illustrated embodiment, the heater system 230 includes a preheater cartridge heater 230PH, a reactor cartridge heater 230R, and a temperature sensor thermocouple 230T. In FIG. 2A, the preheater cartridge heater 230PH and reactor cartridge heater 230R are shown inserted into holes formed in the bulk of the housing 252; and FIG. 2B shows them exploded from those holes. The temperature sensor thermocouple 230T is bonded to a top face of the housing 252. Note that the reactor cartridge heater 230R and its insertion hole in the housing 252 are obscured by coupling 270 in the view of FIG. 2A.

Generally, the controller 105 powers the preheater cartridge heater 230PH and reactor cartridge heater 230R in order to maintain the housing at greater than 100° C. and preferably greater than 100° C., such as 125° C. for EO oxidation and removal. The controller 105 monitors the thermocouple 230T in order to provide a stable, feedback controlled, temperatures.

The valves 220-1, 220-2 in the current design are pneumatically actuated to allow them to operate properly at higher temperatures. An 80 psig ($N_2$ or CDA—Clean Dry Air) stream is utilized to actuate the valves and is controlled by a single stage pressure regulator that is controlled by the controller 105.

Figure 3:
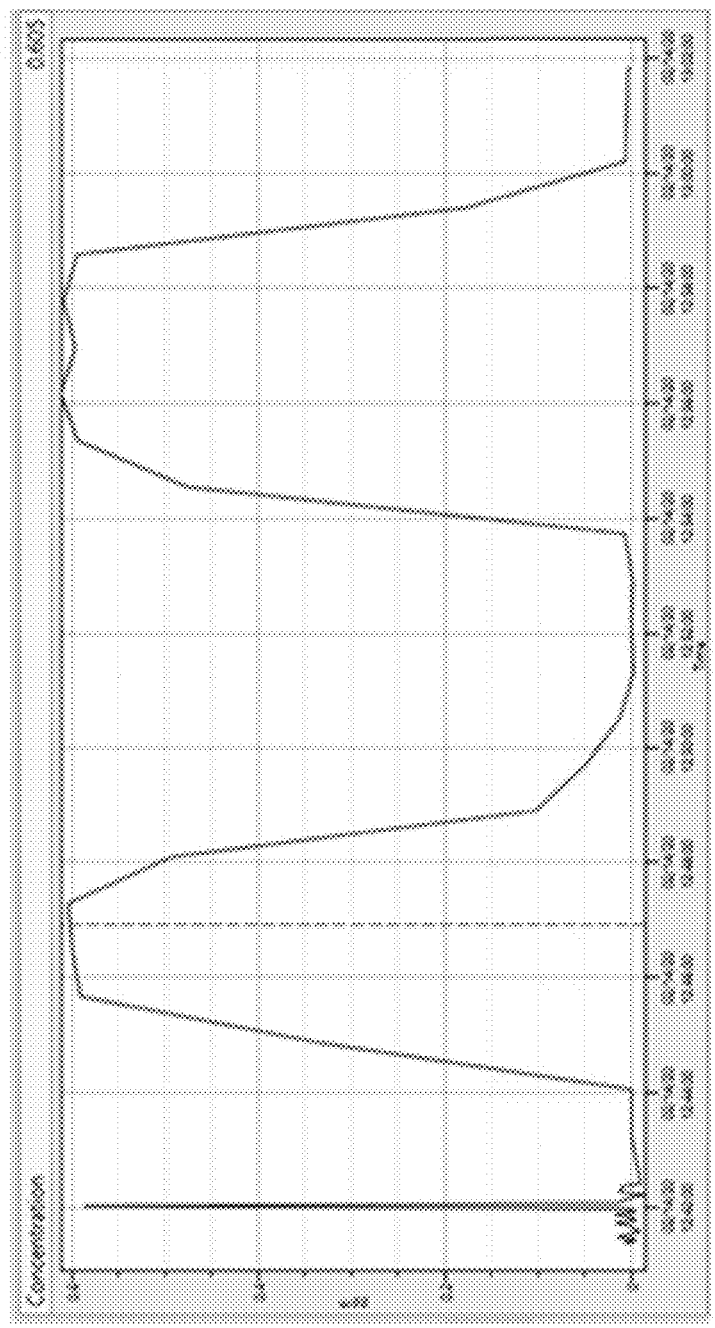
FIG. 3 is a plot of concentration detected the showing the operation of the reactor.

FIG. 3 is a plot of concentration detected the spectrometer 110 and presented by the controller 105 over time. Here, a continuous flow of 600 ppb EO was provided in the sample stream 10. The peaks and troughs are associated with the controller 105 switching between the reactor path 210 and the bypass path 212, respectively. At the beginning of the trace the sample gas is passed through the reactor (oxidizer mode) to oxidize all the EO, then the gas stream is switched to bypass to measure the EO, it is then switched between reactor and bypass another time to demonstrate the ability of the reaction device 200 to remove the EO from the sample stream.

The removal of the EO from a sample stream allows the controller 105 to create an interference spectrum for the sample matrix near-identical to the sample stream for usage in the regression algorithm.

Both water and methane are present in ambient air and both interfere spectrally in the infrared spectral region with EO, as such, having two interference spectra (along with the EO calibration spectra) with varying amounts of each interference can help improve the EO analysis (ie. 2 equations—2 unknowns).

This component removal concept could be utilized for nearly any analyte (ie. HAPs like Benzene, Toluene Xylenes in ambient air) where the interferences (water, methane and carbon dioxide) are less reactive than the analyte of interest and the resultant sample gas is measured through an optical technique.

Other methodologies can be employed by the reactor device 200 besides a catalytic oxidizer, such as a furnace operating at high temperature, a UV source or an additional reaction gas to remove the analyte of interest.

The reactor device 200 employing a thermal oxidizer or furnace reactor could also be used to remove interferences that are more reactive than the analyte(s) of interest such that the analyte can be measured directly without the presence of the interference. An example of this application would be the removal of oxygenated hydrocarbons in biogas to measure siloxane contamination. In most biogas streams there are high levels of oxygenated hydrocarbons that spectrally overlap with the strongest siloxane absorption bands making their quantification difficult. If these gases were removed, it would allow for direct measurement without the need for separation such as gas chromatography.

Figure 4:
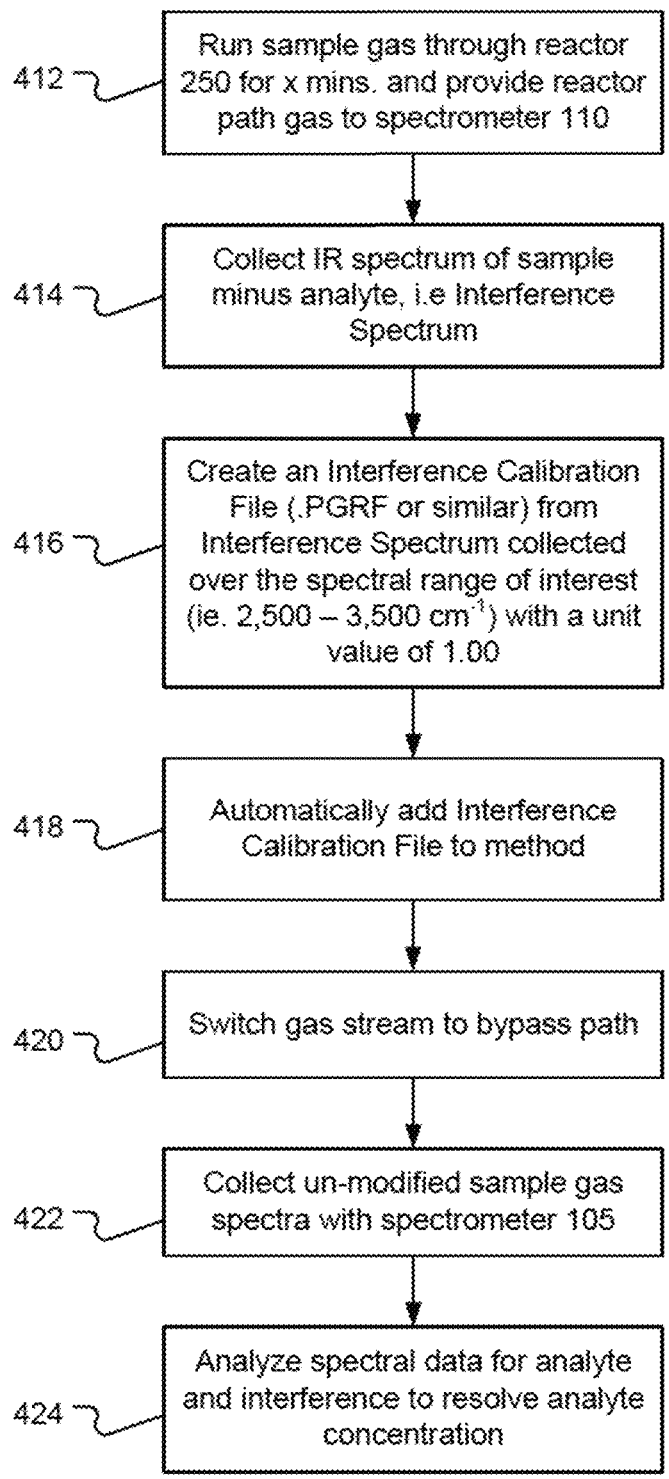
FIG. 4 is a flow diagram showing the operations performed by the controller and the control of the gas analysis system for a basic interference spectrum collection and analysis.

FIG. 4 is a flow diagram showing the operations performed by the controller 105 and the control of the gas analysis system 100 for a basic interference spectrum collection and analysis.

In step 412, the sample gas is directed through the reactor 250 for a specified period of time. Typically, this is at least one minute and typically several minutes. This is effected by the controller 105 controlling the automated valve system 222 to direct the gas through the reactor path 210 and then to the spectrometer 110.

At the same time, in step 414, the spectrometer 110 collects infrared spectra of the sample matrix since the analyte has been reacted in the reactor 250. The controller then determines the interference spectrum.

In step 416, the controller 105 uses the collected interference spectra to create an interference calibration file. If bandlimited analysis is be used, and where the analyte is EO, then the calibration file covers the spectral range of interest (ie. 2,500-3,500 cm$^{-1}$) with a unit value of 1.00. And, in step 418, the controller 105 automatically adds the interference calibration file to the method.

In some cases, the controller averages the interference spectra to reduce noise in a regression analysis. If the interference gases are rapidly changing it may not make sense to co-add or spectrally average these data, however. Thus, the controller 105 chooses not to average or average only if the data are stable. Since there are spectral non-linearity (not detector non-linearity), it is impossible to know in advance if the spectral will co-add properly since they may be fundamentally different at varying concentrations.

In more detail, in some implementations of steps 416 and 418, the controller 105 measures the spectra of the reacted sample stream in step 414 at the spectrometer's fastest rate (e.g., 1 spectrum per second). Then the controller 105 compares the sample spectra to each other. If they are close enough in concentration, such as within 5% of the ppm methane level or 5% of the % water level, the spectra are co-added. Then, the controller 105 collects further spectra and then again co-adds those to the current average spectra if they are also close enough in concentration. This continues until concentration is different by x % or 60 co-adds are obtained. This averaged interference spectrum is then added to method in step 418.

In more detail, in other implementations of steps 416 and 418, the controller 105 measures the interference spectra again at the spectrometer's its fastest rate. The first two samples, Sample1, Sample2, are compared against each other. If they are close enough in concentration, then Sample1, Sample2 are co-added. On the other hand, if they are sufficiently different, parallel coadd is started. Then, more samples, Sample3, are/is created and compared to Sample1 and Sample2, if it is close to either, the new spectra are coadded, or if they are sufficiently different, the two new samples furthest apart are added to a third group. This process is repeated for more interference spectra such as 60 sample points. Ultimately, the two averaged data sets furthest apart in concentration or two with most coadds are added to the method.

Then, in step 420, the controller 105 controls the automated valve system 222 switch to the bypass path 212 and provide the sample gas directly to the spectrometer 110.

Finally, in steps 422 and 424, the controller collects the spectra from the spectrometer 110 and analyzes the spectral data for analyte employing the interference spectra and the calibration file in order to determine the analyte concentration.

Other gases can be added as well including pure component calibrations present in the interference spectrum to make small improvements in the analysis. This can include pure component water and methane calibration spectra as well as the interference spectra. Component calibrations for ethylene, propylene and propylene oxide, which might also be present, can further be added.

This procedure is better than using the interference spectrum as a background since the interference spectrum can then be regressed, and the % of interference can be determined and removed. In more detail, in the typical operation of a FTIR, a background is taken that removes the instrument response function to produce a zero line or a 100% T line from which to measure the analyte. This could be applied here by having the gas flow through the reactor and using the resulting spectra as the background. Then, the sample gas is flowed through the bypass and the compound of interest is measured. Then, the controller just uses the pure gases, water, methane, ethylene, ethylene oxide, propylene, and propylene oxide spectra to measure the EO. So, the interference gases are only measuring the difference in their concentration from when the Background was obtained. This is useful especially when the AutoRef function of the FTIR 110 is employed. It is preferable to put all the compounds in the matrix along with the interference spectrum (which removes most of the spectral features) and can be scaled by the regression analysis. So, if the water went down by 1%, the regression would use 0.99× this spectrum. If water were the only component in the interference spectrum.

Figure 5:
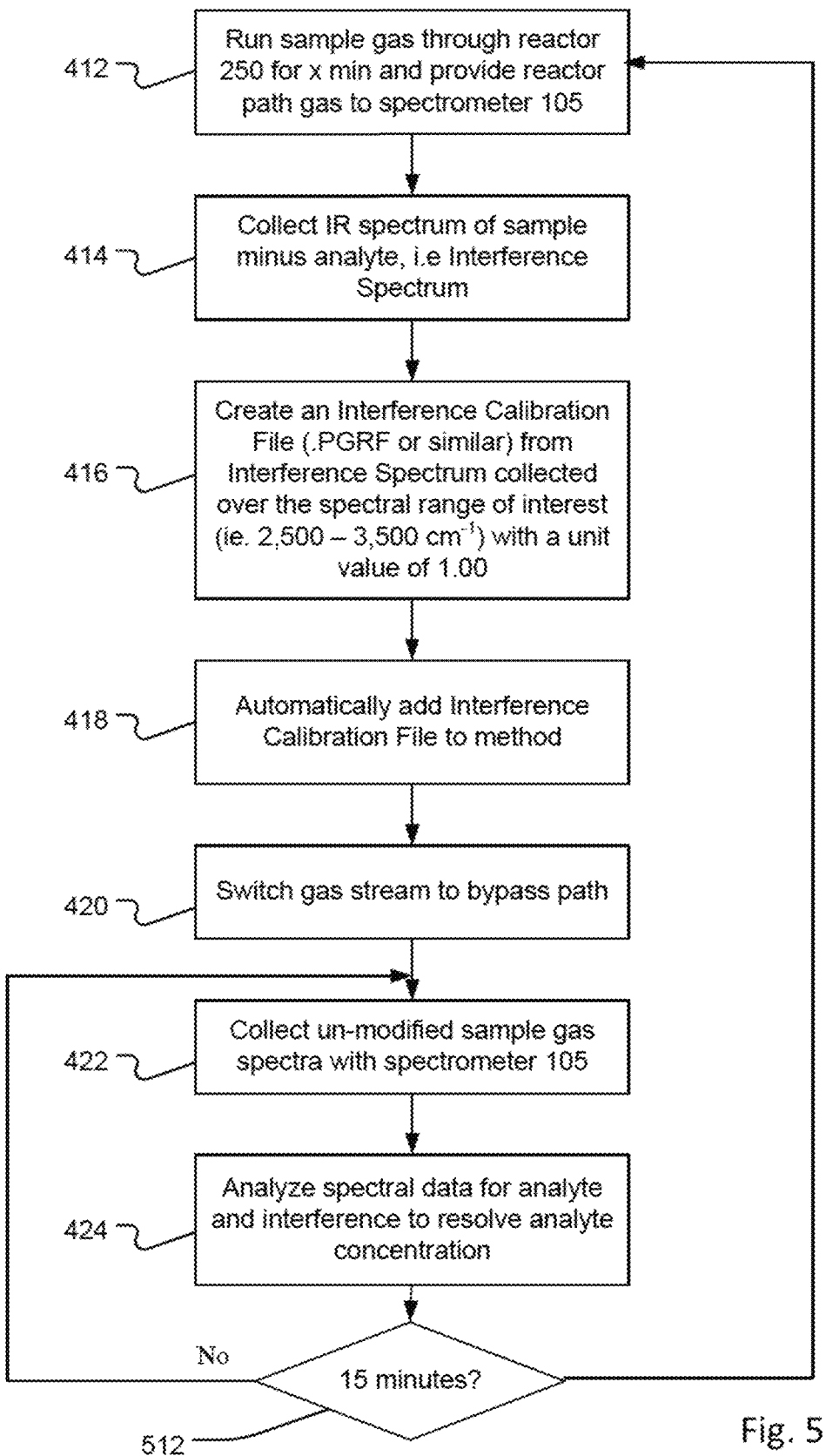
FIG. 5 is a flow diagram showing the operations performed by the controller and the control of the gas analysis system for interference spectrum collection and analysis where it periodically collects a new interference spectra and creates a new calibration file.

FIG. 5 is a flow diagram showing the operations performed by the controller 105 and the control of the gas analysis system 100 for interference spectrum collection and analysis where it periodically collects a new interference spectra and creates a new calibration file.

In more detail, in the operation the controller goes through the process of creating a new calibration file after the expiration of a defined time period, such as 15 minutes, as determined in step 512. Otherwise flow repeats to again perform steps 422, 424.

Figure 6:
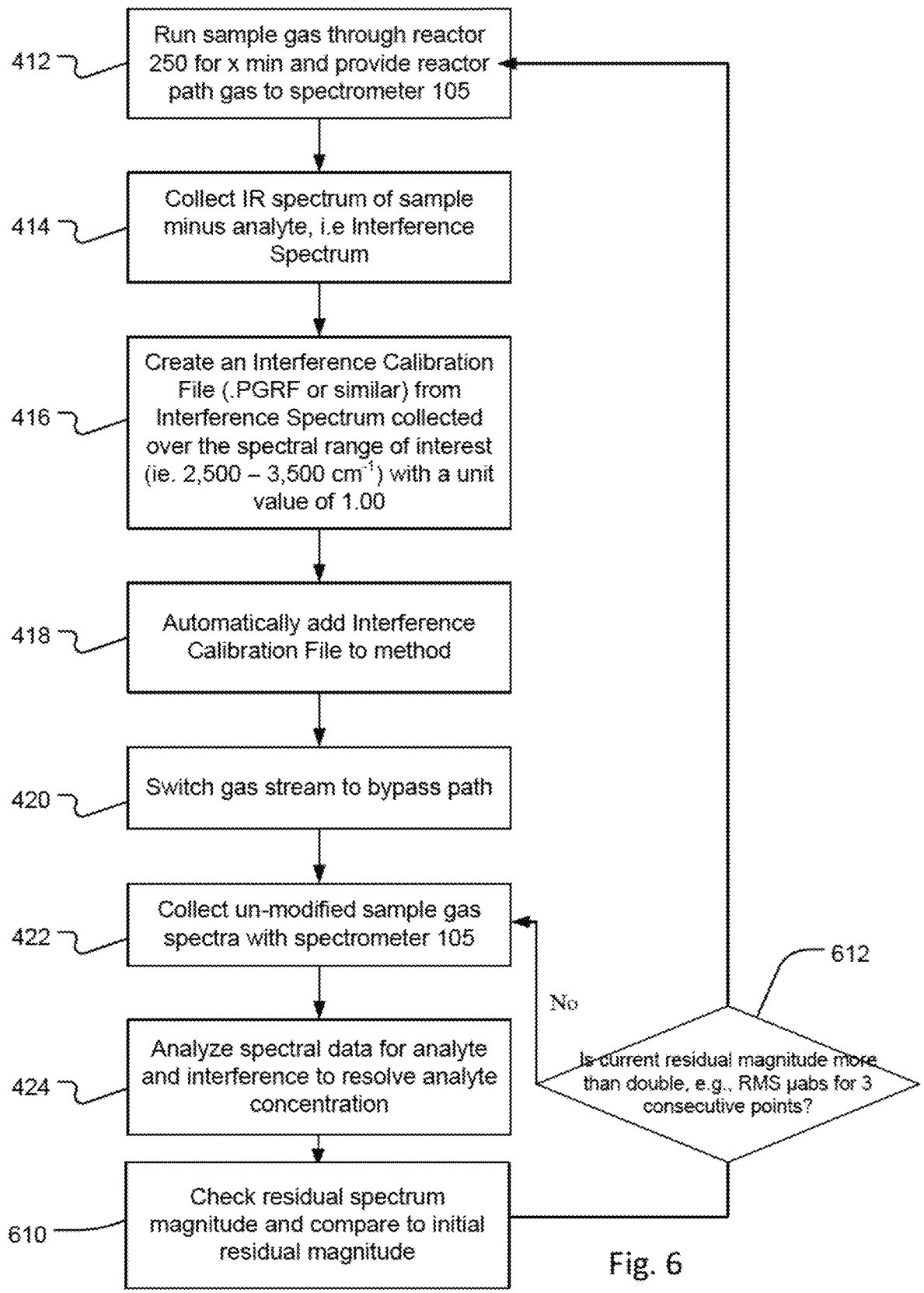
FIG. 6 is a flow diagram showing the operations performed by the controller and the control of the gas analysis system for interference spectrum collection and analysis where it uses a residual spectrum to determine when to collect a new interference spectra and creating a new calibration file.

FIG. 6 is a flow diagram showing the operations performed by the controller 105 and the control of the gas analysis system 100 for interference spectrum collection and analysis where it uses a residual spectrum to determined when to collect a new interference spectra and create a new calibration file.

In more detail, in the operation, the controller checks the residual spectrum magnitude in step 610 and compares that current residual spectrum to the residual spectrum first determined after the creating of a new calibration file. The residual spectrum is calculated by the controller 105 by subtracting the sample spectrum by all the regressed components times their concentration factor. So, if the reference spectrum is exactly the same intensity as the sample spectrum, the factor would be 1. If the reference spectrum were half the intensity the factor would be ~2. The remaining residual spectrum is generally just noise and the RMS noise can be measured to determine if it exceeds a certain level (interference spectrum is no longer matching well enough) like 2 or 3× the original RMS from the first sample point after the interference spectrum collection.

Then, in step 612, if current residual magnitude more than double, e.g., RMS μabs for 3 consecutive points, then the process returns to create a new calibration file.

On the other hand, if current residual magnitude did not exceed double, e.g., RMS μabs for 3 consecutive points, then flow returns to step 422 and the unreacted sample stream continues to be tested.

Figure 7:
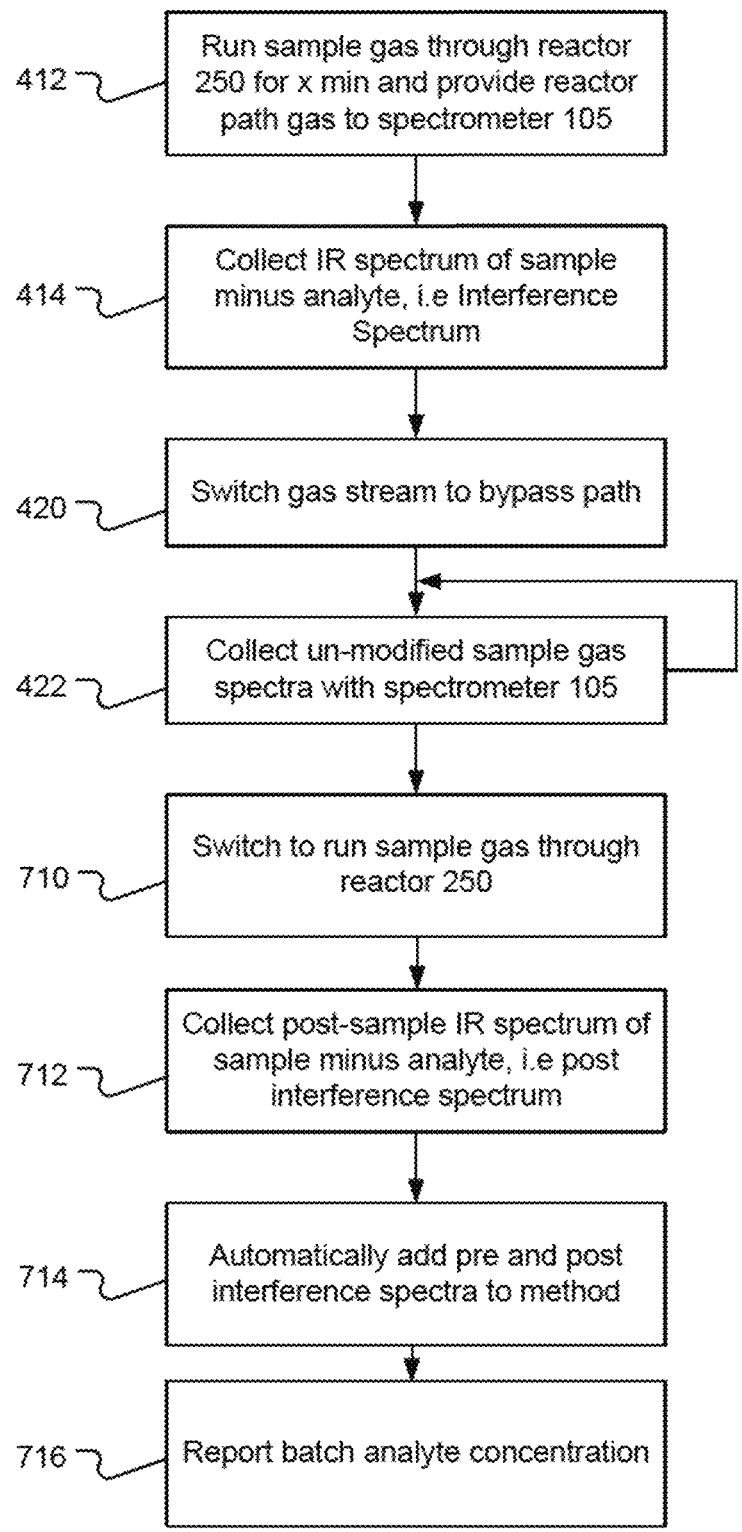
FIG. 7 is a flow diagram showing the operations performed by the controller and the control of the gas analysis system for interference spectrum collection and analysis using batch mode analysis.

FIG. 7 is a flow diagram showing the operations performed by the controller 105 and the control of the gas analysis system 100 for interference spectrum collection and analysis where it uses batch mode analysis.

Here, after collecting the sample gas spectra a predetermined number of times or for a predetermined period of time, the controller switches from the bypass path 212 back to the reactor path 210 in step 710.

Then, in step 712 the controller collects post-sample IR spectra of the sample minus the analyte from the reactor path 210.

Then the controller uses both the pre and post interference spectra to the method in step 714 and reports the batch analyte concentration in step 716.

While this invention has been particularly shown and described with references to preferred embodiments thereof, it will be understood by those skilled in the art that various changes in form and details may be made therein without departing from the scope of the invention.

What is claimed is:

1. A gas analysis system, comprising:
a spectrometer for analyzing gas;
a switched reaction device for switching between providing a sample stream to the spectrometer and providing a reacted sample stream to the spectrometer, the switched reaction device including an input line, an output line, a first path, and a second path, the input line positioned downstream of the sample stream, the output line positioned downstream of the input line and upstream of the spectrometer, the first path coupling the input line to the output line through a reactor, and the second path coupling the input line to the output line, wherein the second path avoids the reactor, wherein the output line is in fluid communication with the spectrometer; and
a controller using the reacted sample stream to create spectra for analyzing the sample stream.

2. The system of claim 1, wherein the spectrometer analyzes the gas at negative or positive atmospheric pressures.

3. The system of claim 1, wherein, when the switched reaction device provides the sample stream to the spectrometer, the switched reaction device provides the reacted sample stream to an exhaust.

4. The system of claim 1, wherein the switched reaction device comprises a preheater for heating the sample stream before flowing into the reactor.

5. The system of claim 1, wherein the switched reaction device comprises the reactor, which is a thermal catalytic oxidizer reactor or furnace reactor to remove an interfering gas or the analyte by oxidization.

6. The system of claim 1, wherein the controller operates the system in a batch mode in which interference spectra are collected before and after spectra of the sample stream.

7. The system of claim 1, wherein the spectrometer is an infrared absorption spectrometer.

8. The system of claim 1, wherein the spectrometer is a mass spectrometer, ion mobility spectrometer, electrochemical sensor, or gas chromatograph.

9. The system of claim 1, wherein the sample stream includes an analyte of interest, and the analyte of interest is removed in the reacted sample stream.

10. The system of claim 9, wherein the analyte of interest includes ethylene oxide.

11. The system of claim 1, wherein the controller further controls the switching between providing the sample stream to the spectrometer and providing a reacted sample stream to the spectrometer based on a predetermined period of time.

12. The system of claim 1, wherein the controller further controls the switching between providing the sample stream to the spectrometer and providing a reacted sample stream to the spectrometer based on a residual spectrum determined based on a spectrum of the sample stream and a calibration spectrum.

13. The system of claim 1, further comprising a chiller upstream of the switched reaction device for controlling a moisture concentration in a sample.

14. The system of claim 1, further comprising a pressurization pump upstream of the switched reaction device for controlling a moisture concentration in a sample.

* * * * *